United States Patent [19]
Eicken et al.

[11] 4,235,928
[45] Nov. 25, 1980

[54] SUBSTITUTED CYANAMIDES AND THEIR USE AS FUNGICIDES

[75] Inventors: Karl Eicken, Wachenheim; Peter Plath, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 99,017

[22] Filed: Nov. 30, 1979

[30] Foreign Application Priority Data

Dec. 18, 1978 [DE]  Fed. Rep. of Germany ....... 2854600

[51] Int. Cl.³ .................... A01N 47/12; C07C 125/08; C07C 121/78

[52] U.S. Cl. ..................... 424/300; 424/266; 424/270; 424/272; 424/275; 424/283; 424/285; 260/345.7 R; 260/345.8 R; 260/347.3; 260/347.4; 260/465 D; 546/323; 548/128; 548/131; 548/200; 548/236; 548/248; 549/70

[58] Field of Search .................... 260/465 D; 424/300, 424/324

[56] References Cited

U.S. PATENT DOCUMENTS 3,954,992  5/1976  Davidson ............................ 424/287

OTHER PUBLICATIONS

Chemical Week, Jun. 1972, p. 46.

Primary Examiner—Henry R. Jiles
Assistant Examiner—Bernard Dentz
Attorney, Agent, or Firm—Keil & Witherspoon

[57] ABSTRACT

New, substituted cyanamides, processes for the manufacture thereof, and fungicides containing these compounds.

3 Claims, No Drawings

SUBSTITUTED CYANAMIDES AND THEIR USE AS FUNGICIDES

The present invention relates to new and valuable substituted cyanamides, processes for the manufacture thereof, and fungicides containing these compounds.

U.S. Pat. No. 3,954,992 discloses that cyanacetamide derivatives, e.g., 2-cyano-N-(ethylaminocarbonyl)-2-methoxyiminoacetamide, have a fungicidal action on lower fungi. The use of N-trichloromethylthiotetrahydrophthalimide for combating fungi has also been disclosed (Chemical Week, June 21, 1972, p. 46).

We have found that substituted cyanamides of the formula

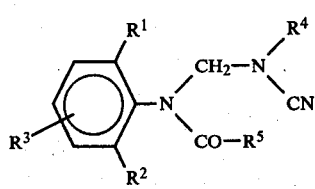

where $R^1$ denotes $C_1$-$C_4$-alkyl or $C_1$-$C_4$-alkoxy, $R^2$ denotes hydrogen, $C_1$-$C_4$-alkyl, $C_1$-$C_4$-alkoxy or halogen, $R^3$ denotes hydrogen, $C_1$-$C_4$-alkyl or halogen, $R^4$ denotes $C_1$-$C_6$-alkoxycarbonyl, $C_3$-$C_4$-alkenoxycarbonyl, $C_1$-$C_6$-alkylthiocarbonyl, or cyano, and $R^5$ denotes $C_1$-$C_6$-alkyl which is unsubstituted or substituted by lower alkoxy, alkylthio, cyano or by halogen; unsubstituted or halogen-substituted $C_2$-$C_5$-alkenyl; $C_2$-$C_4$-alkynyl; $C_3$-$C_7$-cycloalkyl; a heterocyclic radical which is unsubstituted or substituted by lower alkyl or halogen and which contains one oxygen, one sulfur or one nitrogen atom, or up to two nitrogen atoms and one oxygen atom, or up to two nitrogen atoms and one sulfur atom; or $R^5$ denotes unsubstituted phenyl or phenyl substituted by from one to three identical or different substituents selected from the group consisting of fluorine, chlorine, bromine, trifluoromethyl, cyano, nitro, $C_1$-$C_4$-alkyl, and $C_1$-$C_4$-alkoxy, have a good fungicidal action on phytopathogenic fungi.

We have further found that substituted cyanamides are obtained by reaction of an N-halomethylanilide of the formula

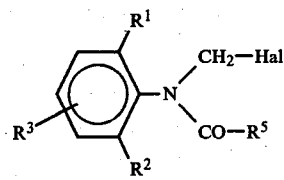

where $R^1$, $R^2$, $R^3$ and $R^5$ have the meanings given above and Hal denotes halogen, especially chlorine and bromine, with a cyanamide of the formula

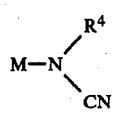

where $R^4$ has the above meanings and M denotes hydrogen, an alkali metal or tetraalkylammonium, in the presence or absence of an acid binder and of a solvent inert to the reactants.

By alkyl and the alkyl moiety of alkoxy in radicals $R^1$, $R^2$, $R^3$, $R^4$ and $R^5$, we mean—depending on the number of carbon atoms specified—for example the following groups: methyl, ethyl, n-propyl, isopropyl, n-butyl, isobutyl, sec-butyl, tert-butyl, pentyl and hexyl, and isomers thereof.

As alkenyl, for instance vinyl, allyl, methallyl and pentenyls may be particularly mentioned. As $C_2$-$C_4$-alkynyl, for example ethynyl, propargyl and but-2-ynyl may be particularly mentioned.

As cycloalkyl, for example cyclopropyl, cyclobutyl, cyclopentyl and cyclohexyl may be particularly singled out.

Examples of halogen are fluorine, chlorine and bromine.

Preferred heterocyclic radicals at $R^5$ are 5- to 6-membered, e.g., furan, thiophene, oxazole, isoxazole, thiazole, oxadiazole, thiodiazole, tetrahydrofuran, 2,3-dihydropyran and pyridine, and are unsubstituted or substituted by methyl and/or halogen.

Particularly suitable examples of substituted phenyl for $R^5$ are monosubstituted phenyls, such as fluorophenyl, chlorophenyl, bromophenyl, trifluoromethylphenyl, tolyl, anisyl, and nitrophenyl; and disubstituted phenyls, such as dichlorophenyl, difluorophenyl, fluorochlorophenyl, dimethylphenyl, dimethoxyphenyl, methylfluorophenyl, methylchlorophenyl, methylbromophenyl, methoxychlorophenyl, methyltrifluoromethylphenyl, and chlorotrifluoromethylphenyl.

The reactions can be carried out in the presence or absence of solvents inert to the reactants. Examples of suitable solvents are aromatic hydrocarbons, such as toluene and xylene; halogenated hydrocarbons, such as chlorobenzene, chloroform, methylene chloride and methyl chloride; ethers, such as tetrahydrofuran and dioxane; nitriles, such as acetonitrile; N,N-dialkylamides, such as dimethylformamide; sulfones, such as dimethyl sulfoxide; ketones, such as acetone; aliphatic esters, such as ethyl acetate; and mixtures of these solvents. The reaction temperature is from 0° to 150° C., preferably from 20° to 100° C.

If a cyanamide of the formula III in which M denotes hydrogen is reacted, it is advantageous to use an acid binder. Suitable binders are tertiary amines, e.g., triethylamine, pyridine and substituted pyridines, and inorganic bases, e.g., oxides, hydroxides, carbonates and bicarbonates of alkali metals.

We have further found a special method for the manufacture of cyanamide compounds of the formula I, wherein an N-halomethylanilide of the formula

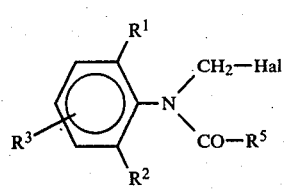

where $R^1$, $R^2$, $R^3$ and $R^5$ have the above meanings and Hal denotes chlorine or bromine, is reacted with a cyanamide of the formula

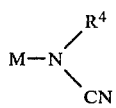

where R⁴ has the above meanings and M denotes an alkali metal, in a two-phase system (the one phase being water and the other a solvent immiscible with the aqueous phase and inert to the reactants) and in the presence of a phase transfer catalyst. If desired, the reaction may also be carried out in a two-phase system in the presence of a phase transfer catalyst without the addition of water—the cyanamide of the formula III is then suspended as solid phase in the water-immiscible solvent.

The water-immiscible solvent is preferably an aromatic or a halogenated hydrocarbon. The phase transfer catalyst is employed for instance in amounts of from 0.5 to 30 mole%, based on N-halomethylanilide of the formula II used.

The reaction is carried out at from 0° to 100° C., preferably from 10° to 50° C.

Suitable phase transfer catalysts are onium compounds, e.g., quaternary ammonium and phosphonium compounds, and macrocyclic polyethers. Examples of quaternary ammonium compounds are tetrabutylammonium bisulfate, tetrapentylammonium chloride, tetraoctylammonium chloride, tripropylbutylammonium chloride, tricaprylylmethylammonium chloride, hexadecyl-trimethylammonium chloride, distearyl-dimethylammonium chloride, dibenzyldimethylammonium methyl sulfate, dimethyldodecyl-benzylammonium chloride, benzyltrimethylammonium chloride, benzyltriethylammonium chloride, and 2-hydroxyethyltrimethylammonium chloride; examples of quaternary phosphonium compounds are tributylmethylphosphonium bromide, hexadecyl-tributylphosphonium bromide, ethyltriphenylphosphonium bromide, tetraphenylphosphonium bromide, and the hydroxides of these onium compounds.

Examples of macrocyclic polyethers are 15-crown-5, 18-crown-6, dibenzo-18-crown-6 and dicyclohexyl-18-crown-6 (crown ethers).

To prepare the new compounds, at least 1 mole of cyanamide of the formula III is used per mole of N-halomethylanilide of the formula II.

To isolate the compounds of the formula I, for instance the halide which has formed is if desired filtered off, the filtrate is evaporated and the residue is dissolved in an organic water-immiscible solvent. The organic phase is then washed with water, dried and concentrated in vacuo. The product of the formula I which is obtained is in many cases pure; if necessary, it can be further purified by recrystallization or chromatography, for example with silica gel.

In the two-phase manufacturing process, the organic phase is separated (or the undissolved material is filtered off) after completion of the reaction, washed with water and dried, and the active ingredient of the formula I is isolated as described above.

Some of the N-halomethylanilides used as starting materials are known (U.S. Pat. No. 3,637,847); others may be prepared in conventional manner by reaction of correspondingly substituted phenylazomethines with acid chlorides of the formula R⁵-CO-Hal, R⁵ having the above meanings and Hal denoting halogen.

The cyanamide compounds of the formula III are known, for example cyanocarbamic acid esters (German 2,474,453, German Laid-Open Application DE-OS 1,795,849), cyanocarbamic acid thiol esters (Yuki Cosei Kagaku Kyokai Shi, 1971, 29, (1) 67 (CA: 74, 140877 u)) and dicyanimide (Liebigs Ann. Chem., 427, 1, 1922; J. Chem. Soc., C, 1970, 875).

Individual examples of cyanamide compounds, and salts thereof, suitable as starting products are as follows:
  cyanocarbamic acid methyl ester and its sodium, potassium and tetramethylammonium salts;
  cyanocarbamic acid ethyl ester and its sodium, potassium and tetramethylammonium salts;
  cyanocarbamic acid n-propyl ester and its sodium, potassium, and tetramethylammonium salts;
  cyanocarbamic acid isopropyl ester and its sodium and potassium salts;
  cyanocarbamic acid n-butyl ester and its sodium and potassium salts;
  cyanocarbamic acid sec-butyl ester and its sodium and potassium salts;
  cyanocarbamic acid n-hexyl ester and its sodium and potassium salts;
  cyanocarbamic acid methylthiol ester and its sodium, potassium and tetramethylammonium salts;
  cyanocarbamic acid ethylthiol ester and its sodium, potassium and tetraethylammonium salts;
  cyanocarbamic acid n-propylthiol ester and its sodium and potassium salts;
  cyanocarbamic acid isopropylthiol ester and its sodium and potassium salts; and
  dicyanimide; especially its sodium, potassium and tetramethylammonium salts.

The following examples illustrate the preparation of the new cyanamide compounds of the formula I and of the starting materials of the formula II.

In the examples, parts by weight bear the same relationship to parts by volume as kilograms to liters.

EXAMPLE A

At 5° to 10° C. and while stirring, 315 parts by volume of a toluene solution containing 1 mole of 2,6-dimethylphenylazomethine (U.S. Pat. No. 3,637,847) was dripped, with cooling, into a solution of 130.5 parts by weight of 2-furancarboxylic acid chloride in 100 parts by volume of toluene; the mixture was then stirred for 10 hours at room temperature. After cooling, filtration and drying in vacuo, there was obtained 198 parts by weight of N-chloromethylfuran-2-carboxylic acid-2',6'-dimethylanilide of melting point 124°–126° C.

The following N-halomethylanilides of the formula II may be prepared analogously:

| R¹ | R² | R³ | Hal | R⁵ | m.p. °C. |
|---|---|---|---|---|---|
| CH₃ | CH₃ | H | Cl | CH₃ | solid mass |
| CH₃ | C₂H₅ | H | Cl | CH₃ | solid mass |
| C₂H₅ | C₂H₅ | H | Cl | CH₃ | oil |
| CH₃ | CH₃ | H | Cl | C₂H₅ | oil |
| CH₃ | C₂H₅ | H | Cl | C₂H₅ | oil |
| C₂H₅ | C₂H₅ | H | Cl | C₂H₅ | oil |
| CH₃ | CH₃ | H | Cl | CH(CH₃)₂ | |

-continued

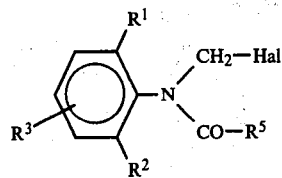

| R¹ | R² | R³ | Hal | R⁵ | m.p. °C. |
|---|---|---|---|---|---|
| CH₃ | C₂H₅ | H | Cl | CH(CH₃)₂ | |
| C₂H₅ | C₂H₅ | H | Cl | CH(CH₃)₂ | 75–76 |
| C₂H₅ | C₂H₅ | H | Cl | C(CH₃)₃ | oil |
| CH₃ | CH₃ | H | Cl | CH(Cl)CH₃ | 95 |
| C₂H₅ | CH₃ | H | Cl | CH(Cl)CH₃ | |
| C₂H₅ | C₂H₅ | H | Cl | CH(Cl)CH₃ | |
| CH₃ | CH₃ | 2-CH₃ | Cl | CH(Cl)CH₃ | |
| CH₃ | C₂H₅ | H | Cl | CH₂—CH₂Cl | viscous oil |
| CH₃ | CH₃ | H | Cl | CH₂—CH₂Cl | |
| CH₃ | CH₃ | H | Cl | CH₂—CH₂—CH₂Cl | |
| CH₃ | CH₃ | H | Cl | CHCl₂ | 102–104 |
| CH₃ | CH₃ | CH₃ | Cl | CHCl₂ | |
| CH₃ | C₂H₅ | H | Cl | CHCl₂ | 88–90 |
| CH₃ | CH₃ | H | Cl | CCl₃ | oil |
| CH₃ | CH₃ | H | Cl | CH=CH₂ | |
| CH₃ | CH₃ | H | Cl | C≡CH | |
| CH₃ | CH₃ | H | Cl | C(CH₃)=CH₂ | 91–92 |
| CH₃ | CH₃ | H | Cl | C(Cl)=CH₂ | |
| CH₃ | CH₃ | H | Cl | CH=CCl₂ | |
| CH₃ | CH₃ | H | Cl | CCl=CCl₂ | |
| CH₃ | CH₃ | H | Cl | cyclopropyl | 82 |
| CH₃ | C₂H₅ | H | Cl | cyclopropyl | oil |
| C₂H₅ | C₂H₅ | H | Cl | cyclopropyl | oil |
| CH₃ | CH₃ | H | Cl | cyclobutyl | |
| CH₃ | CH₃ | H | Cl | cyclohexyl | |
| CH₃ | C₂H₅ | H | Cl | cyclohexyl | |
| C₂H₅ | C₂H₅ | H | Cl | cyclohexyl | 97–100 |
| CH₃ | CH₃ | H | Cl | CH₂OCH₃ | 70 |
| CH₃ | CH₃ | CH₃ | Cl | CH₂OCH₃ | |
| CH₃ | C₂H₅ | H | Cl | CH₂OCH₃ | |
| C₂H₅ | C₂H₅ | H | Cl | CH₂OCH₃ | oil |
| CH₃ | CH₃ | H | Cl | CH₂SCH₃ | crystalline mass |
| CH₃ | C₂H₅ | H | Cl | CH₂SCH₃ | 127 |
| C₂H₅ | C₂H₅ | H | Cl | CH₂SCH₃ | oil |
| CH₃ | CH₃ | H | Cl | CH₂—CN | |
| CH₃ | CH₃ | H | Cl | phenyl | 133 |
| CH₃ | C₂H₅ | H | Cl | phenyl | |
| C₂H₅ | C₂H₅ | H | Cl | phenyl | 98–99 |
| CH₃ | CH₃ | H | Cl | 2-F-phenyl | 86–88 |

-continued

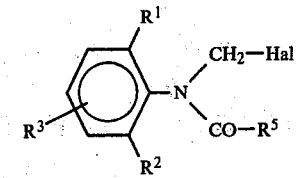

| R¹ | R² | R³ | Hal | R⁵ | m.p. °C. |
|---|---|---|---|---|---|
| CH₃ | CH₃ | H | Cl | 3-F-phenyl | 114–116 |
| CH₃ | CH₃ | H | Cl | 4-F-phenyl | 141–143 |
| CH₃ | CH₃ | H | Cl | 2-Cl-phenyl | 93 |
| CH₃ | CH₃ | H | Cl | 3-Cl-phenyl | 145 |
| CH₃ | CH₃ | H | Cl | 4-Cl-phenyl | 120 |
| CH₃ | CH₃ | H | Cl | 2,3-Cl₂-phenyl | 108 |
| C₂H₅ | C₂H₅ | H | Cl | 2,4-Cl₂-phenyl | |
| CH₃ | CH₃ | H | Cl | 3,4-Cl₂-phenyl | 132 |
| CH₃ | CH₃ | H | Cl | 2-CF₃-phenyl | |
| CH₅ | C₂H₅ | H | Cl | 3-CF₃-phenyl | 63–64 |
| CH₃ | CH₃ | H | Cl | 4-CF₃-phenyl | 108–109 |
| C₂H₅ | C₂H₅ | H | Cl | 3-CN-phenyl | 112–114 |
| CH₃ | CH₃ | H | Cl | 2-CH₃-phenyl | 118–119 |
| CH₃ | CH₃ | H | Cl | 4-CH₃-phenyl | 119–120 |
| CH₃ | CH₃ | H | Cl | 3-OCH₃-phenyl | |
| CH₃ | CH₃ | H | Cl | 2-O₂N-phenyl | 205–207 |

-continued

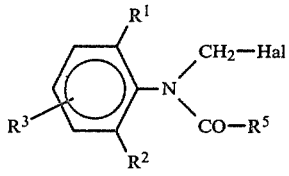

| R¹ | R² | R³ | Hal | R⁵ | m.p. °C. |
|---|---|---|---|---|---|
| CH₃ | CH₃ | H | Cl | 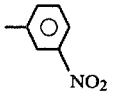 | 152–154 |
| CH₃ | CH₃ | H | Cl | 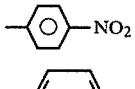 | |
| CH₃ | CH₃ | H | Cl | 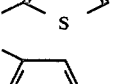 | 94–97 |
| CH₃ | CH₃ | H | Cl | 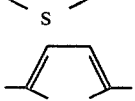 | 120–121 |
| CH₃ | CH₃ | H | Cl | 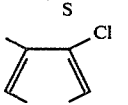 | |
| CH₃ | CH₃ | H | Cl | 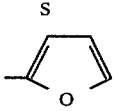 | 118 |
| CH₃ | CH₃ | H | Cl | 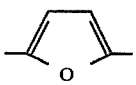 | 124–126 |
| CH₃ | CH₃ | H | Cl | 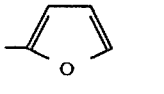 | |
| C₂H₅ | C₂H₅ | H | Cl | 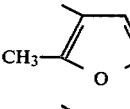 | 69–70 |
| CH₃ | CH₃ | H | Cl | 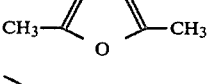 | 68–70 |
| C₂H₅ | C₂H₅ | H | Cl | 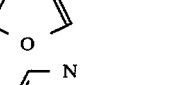 | |
| CH₃ | CH₃ | H | Cl | 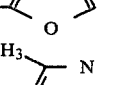 | |
| CH₃ | CH₃ | H | Cl |  | |
| CH₃ | CH₃ | H | Cl | 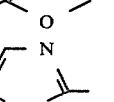 | 83–85 |
| CH₃ | CH₃ | H | Cl | 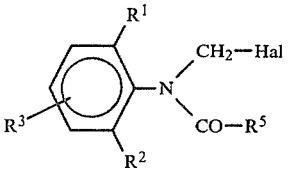 | 106 |
| CH₃ | CH₃ | H | Cl | 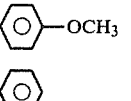 | |

-continued

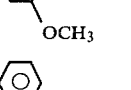

| R¹ | R² | R³ | Hal | R⁵ | m.p. °C. |
|---|---|---|---|---|---|
| CH₃ | CH₃ | H | Cl | 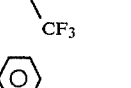 | 92–93 |
| CH₃ | CH₃ | H | Cl | 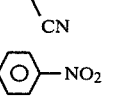 | 107–108 |
| CH₃ | CH₃ | H | Cl | 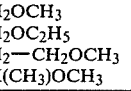 | 105 |
| CH₃ | CH₃ | H | Cl | 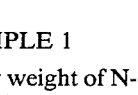 | 118–120 |
| C₂H₅ | C₂H₅ | H | Cl | 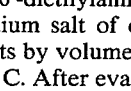 | 118–120 |
| CH₃ | H | 4-Cl | Cl | CH₂OCH₃ | oil |
| CH₃ | CH₃ | H | Cl | CH₂OC₂H₅ | 80–81 |
| CH₃ | CH₃ | H | Cl | CH₂—CH₂OCH₃ | oil |
| CH₃ | CH₃ | H | Cl | CH(CH₃)OCH₃ | oil |

EXAMPLE 1

A mixture of 29.2 parts by weight of N-chloromethyl-furan-2-carboxylic acid-2',6'-diethylanilide and 13.4 parts by weight of the sodium salt of cyanocarbamic acid methyl ester in 120 parts by volume of acetonitrile is stirred for 12 hours at 25° C. After evaporation of the solvent in vacuo, the solvent is dissolved in ethyl acetate and water. The organic phase is dried, the solvent is evaporated, and the residue is triturated with diisopropyl ether; there is obtained 25.5 parts of N-methoxycarbonyl-N-(N'-furyl-2-carbonyl, N'-2',6'-diethylanilinomethyl)-cyanamide of melting point 101°–103° C.

EXAMPLE 2

At 20° to 25° C., a solution of 26.4 parts by weight of N-(chloromethyl)-furan-2-carboxylic acid-2',6'-dimethylanilide in 70 parts by volume of methylene chloride is dripped, with intensive mixing of the phases, into a solution of 12.2 parts by weight of the sodium salt of cyanocarbamic acid methyl ester and 1 part of benzyltriethylammonium chloride in 30 parts by volume of water. After mixing for 6 hours, the organic phase is separated, washed 3 times with water and dried over sodium sulfate. After evaporation of the solvent there is obtained 29.0 parts by weight of N-methoxycarbonyl-N-(N'-furyl-2-carbonyl, N'-2',6'-dimethylanilinomethyl)-cyanamide; after recrystallization from a small amount of methanol, the compound has a melting point of 96°–98° C.

EXAMPLE 3

24.1 parts by weight of N-chloromethylbenzoic acid-2,6-dimethylanilide is dissolved in 100 parts by volume of acetonitrile; 11.8 parts by weight of the sodium salt of cyanocarbamic acid methyl ester is added, and the mixture is stirred at 25° C. for 24 hours. Undissolved matter is filtered off, the filtrate is concentrated in vacuo and the residue is dissolved in methylene chloride and water. The solvent is evaporated from the organic phase and the residue is recrystallized from methanol (100 ml).

There is obtained 18.0 parts by weight of N-methoxycarbonyl-N-(N'-benzoyl, N'-2',6'-dimethylanilinomethyl)-cyanamide of melting point 136° C.

The following compounds are obtained analogously:

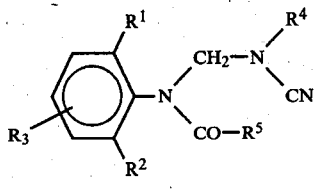

| Compound no. | $R^1$ | $R^2$ | $R^3$ | $R^4$ | $R^5$ | m.p. (°C.) or $n_D^{20}$ |
|---|---|---|---|---|---|---|
| 1 | $CH_3$ | $CH_3$ | H | $CO_2CH_3$ | $CH_3$ | 112–114 |
| 2 | $CH_3$ | $CH_3$ | H | $CO_2C_2H_5$ | $CH_3$ | 78–80 |
| 3 | $CH_3$ | $C_2H_5$ | H | $CO_2CH_3$ | $CH_3$ | |
| 4 | $CH_3$ | $CH_3$ | H | $CO_2CH_3$ | $C_2H_5$ | |
| 5 | $CH_3$ | $C_2H_5$ | H | $CO_2CH_3$ | $C_2H_5$ | |
| 6 | $C_2H_5$ | $C_2H_5$ | H | $CO_2CH_3$ | $C_2H_5$ | |
| 7 | $CH_3$ | $CH_3$ | H | $CO_2CH_3$ | $CH(CH_3)_2$ | |
| 8 | $C_2H_5$ | $C_2H_5$ | H | $CO_2CH_3$ | $CH(CH_3)_2$ | 1.516 |
| 9 | $CH_3$ | $CH_3$ | H | $CO_2CH_3$ | $CH(Cl)CH_3$ | 100 |
| 10 | $CH_3$ | $C_2H_5$ | H | $CO_2CH_3$ | $CH(Cl)CH_3$ | |
| 11 | $CH_3$ | $CH_3$ | H | $COSCH_3$ | $CH(Cl)CH_3$ | |
| 12 | $CH_3$ | $CH_3$ | H | CN | $CH(Cl)CH_3$ | |
| 13 | $CH_3$ | $CH_3$ | H | $CO_2CH_3$ | $CH_2-CH_2Cl$ | oil |
| 14 | $CH_3$ | $CH_3$ | H | $CO_2CH_3$ | $CH_2-CH_2-CH_2Cl$ | |
| 15 | $CH_3$ | $CH_3$ | H | $CO_2CH_3$ | $CHCl_2$ | |
| 16 | $CH_3$ | $C_2H_5$ | H | $CO_2CH_3$ | $CHCl_2$ | |
| 17 | $CH_3$ | $CH_3$ | H | $CO_2C_2H_5$ | $CHCl_2$ | |
| 18 | $CH_3$ | $CH_3$ | H | $CO_2i\text{-}C_3H_7$ | $CHCl_2$ | |
| 19 | $CH_3$ | $CH_3$ | H | $COSCH_3$ | $CHCl_2$ | |
| 20 | $CH_3$ | $CH_3$ | H | $CO_2CH_2$ | $CCl_3$ | |
| 21 | $CH_3$ | $CH_3$ | H | $CO_2CH_3$ | $CH=CH_2$ | 92 |
| 22 | $CH_3$ | $CH_3$ | H | $CO_2CH_3$ | $C\equiv CH$ | |
| 23 | $CH_3$ | $CH_3$ | H | $CO_2CH_3$ | $C(CH_3)=CH_2$ | 90 |
| 24 | $CH_3$ | $CH_3$ | H | $CO_2CH_3$ | $C(Cl)=CH_2$ | |
| 25 | $CH_3$ | $CH_3$ | H | $CO_2CH_3$ | $CH=CCl_2$ | |
| 26 | $CH_3$ | $CH_3$ | H | $CO_2C_2H_5$ | $CCl=CCl_2$ | |
| 27 | $CH_3$ | $CH_3$ | H | $CO_2CH_3$ | ◁ | 106 |
| 28 | $CH_3$ | $C_2H_5$ | H | $CO_2CH_3$ | ◁ | |
| 29 | $C_2H_5$ | $C_2H_5$ | H | $CO_2CH_3$ | ◁ | |
| 30 | $CH_3$ | H | 3-$CH_3$ | $CO_2C_2H_5$ | ◁ | |
| 31 | $CH_3$ | H | 5-$CH_3$ | $CO_2C_2H_5$ | ◁ | |
| 32 | $CH_3$ | H | 5-Cl | $CO_2CH_3$ | ◁ | |
| 33 | $CH_3$ | $CH_3$ | H | $COSCH_3$ | ◁ | |
| 34 | $CH_3$ | $CH_3$ | H | $CO_2CH_3$ | □ | |
| 35 | $CH_3$ | $CH_3$ | H | $CO_2CH_3$ | ⟨H⟩ | |
| 36 | $C_2H_5$ | $C_2H_5$ | H | $CO_2CH_3$ | ⟨H⟩ | viscous |
| 37 | $CH_3$ | $CH_3$ | H | $CO_2CH_3$ | $CH_2OCH_3$ | 74–76 |
| 38 | $CH_3$ | $CH_3$ | 6-$CH_3$ | $CO_2CH_3$ | $CH_2OCH_3$ | |

-continued

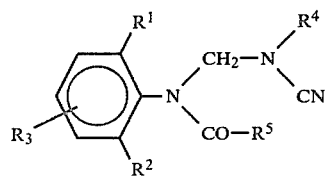

| Compound no. | R¹ | R² | R³ | R⁴ | R⁵ | m.p. (°C.) or $n_D^{20}$ |
|---|---|---|---|---|---|---|
| 39 | $C_2H_5$ | $C_2H_5$ | H | $CO_2CH_3$ | $CH_2OCH_3$ | |
| 40 | $CH_3$ | $CH_3$ | H | CN | $CH_2OCH_3$ | |
| 41 | $CH_3$ | $CH_3$ | H | $CO_2C_2H_5$ | $CH_2OCH_3$ | 86 |
| 42 | $CH_3$ | $CH_3$ | H | $CO_2i-C_3H_7$ | $CH_2OCH_3$ | |
| 43 | $CH_3$ | $CH_3$ | H | $CO-SCH_3$ | $CH_2OCH_3$ | 118 |
| 44 | $CH_3$ | H | 5-$CH_3$ | $CO_2CH_3$ | $CH_2OCH_3$ | |
| 45 | $CH_3$ | H | 4-Cl | $CO_2CH_3$ | $CH_2OCH_3$ | 103 |
| 46 | $CH_3$ | H | 4-$CH_3O$ | $CO_2CH_3$ | $CH_2OCH_3$ | |
| 47 | $CH_3$ | $CH_3$ | H | $CO_2CH_3$ | $CH_2SCH_3$ | |
| 48 | $CH_3$ | $C_2H_5$ | H | $CO_2CH_3$ | $CH_2SCH_3$ | |
| 49 | $C_2H_5$ | $C_2H_5$ | H | $CO_2CH_3$ | $CH_2SCH_3$ | |
| 50 | $CH_3$ | $CH_3$ | H | $COSCH_3$ | $CH_2SCH_3$ | |
| 51 | $CH_3$ | $CH_3$ | H | $CO_2CH_3$ | $CH_2-CN$ | |
| 52 | $CH_3$ | $CH_3$ | H | $CO_2CH_3$ | phenyl | |
| 53 | $CH_3$ | $CH_3$ | H | $CO_2CH_3$ | phenyl | 136 |
| 54 | $CH_3$ | $CH_3$ | H | CN | phenyl | |
| 55 | $CH_3$ | $CH_3$ | H | $CO_2CH_3$ | 2-F-phenyl | 117 |
| 56 | $CH_3$ | $CH_3$ | H | $CO_2CH_3$ | 4-F-phenyl | 145 |
| 57 | $CH_3$ | $CH_3$ | H | $CO_2CH_3$ | 2-Cl-phenyl | oil |
| 58 | $CH_3$ | $CH_3$ | H | $CO_2CH_3$ | 3-Cl-phenyl | 98–101 |
| 59 | $CH_3$ | $CH_3$ | H | $CO_2CH_3$ | 4-Cl-phenyl | 161 |
| 60 | $CH_3$ | $CH_3$ | H | $CO_2CH_3$ | 2,4-Cl₂-phenyl | 90 |
| 61 | $CH_3$ | H | 5-$CH_3$ | $CO_2CH_3$ | 2,4-Cl₂-phenyl | |
| 62 | $CH_3$ | $CH_3$ | H | $COSCH_3$ | 2,4-Cl₂-phenyl | |
| 63 | $CH_3$ | $CH_3$ | H | $CO_2CH_3$ | 3,4-Cl₂-phenyl | 139 |
| 64 | $CH_3$ | $CH_3$ | H | $CO_2CH_3$ | 2-$CF_3$-phenyl | |

-continued $$\begin{array}{c} R^1 \\ \phantom{R^1} \\ R_3 \overset{\displaystyle \diagdown}{\underset{\displaystyle R^2}{\bigcirc}} \overset{\displaystyle CH_2-N\diagdown_{CN}^{R^4}}{\underset{\displaystyle CO-R^5}{N}} \end{array}$$

| Compound no. | $R^1$ | $R^2$ | $R^3$ | $R^4$ | $R^5$ | m.p. (°C.) or $n_D^{20}$ |
|---|---|---|---|---|---|---|
| 65 | $CH_3$ | $CH_3$ | H | $CO_2CH_3$ | –C$_6$H$_4$–CF$_3$ (4-) | |
| 66 | $C_2H_5$ | $C_2H_5$ | H | $CO_2CH_3$ | –C$_6$H$_4$–CN (3-) | |
| 67 | $CH_3$ | $CH_3$ | H | $CO_2CH_3$ | –C$_6$H$_4$–CH$_3$ (2-) | 105–106 |
| 68 | $CH_3$ | $CH_3$ | H | $CO_2CH_3$ | –C$_6$H$_4$–CH$_3$ (3-) | 125–127 |
| 69 | $CH_3$ | $CH_3$ | H | $CO_2CH_3$ | –C$_6$H$_4$–CH$_3$ (4-) | 117–119 |
| 70 | $CH_3$ | $CH_3$ | H | $CO_2CH_3$ | –C$_6$H$_4$–OCH$_3$ (2-) | |
| 71 | $CH_3$ | $CH_3$ | H | $CO_2CH_3$ | –C$_6$H$_4$–NO$_2$ (2-) | |
| 72 | $CH_3$ | $CH_3$ | H | $CO_2CH_3$ | –C$_6$H$_4$–NO$_2$ (3-) | 132–133 |
| 73 | $CH_3$ | $CH_3$ | H | $CO_2CH_3$ | –C$_6$H$_4$–NO$_2$ (4-) | |
| 74 | $CH_3$ | $CH_3$ | H | $CO_2CH_3$ | 2-thienyl | 115–116 |
| 75 | $CH_3$ | $CH_3$ | H | $CO_2C_2H_5$ | 2-thienyl | |
| 76 | $CH_3$ | $C_2H_5$ | H | $CO_2C_2H_5$ | 3-methyl-2-thienyl | |
| 77 | $CH_3$ | $CH_3$ | H | $CO_2CH_3$ | 3-methyl-2-thienyl | 121 |
| 78 | $CH_3$ | $CH_3$ | H | $CO_2CH_3$ | 5-chloro-2-thienyl | |
| 79 | $CH_3$ | $CH_3$ | H | $CO_2CH_3$ | 3-chloro-2-thienyl | 130–132 |

-continued

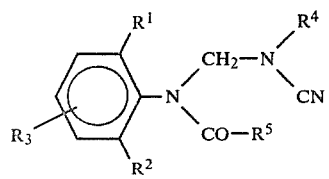

| Compound no. | R¹ | R² | R³ | R⁴ | R⁵ | m.p. (°C.) or $n_D^{20}$ |
|---|---|---|---|---|---|---|
| 80 | CH₃ | CH₃ | H | CO₂CH₃ | 5-methylfuran-2-yl | 96–98 |
| 81 | CH₃ | C₂H₅ | H | CO₂C₂H₅ | 5-methylfuran-2-yl | oil |
| 82 | CH₃ | CH₃ | H | COSCH₃ | 5-methylfuran-2-yl | 121 |
| 83 | CH₃ | CH₃ | H | CN | 5-methylfuran-2-yl | |
| 84 | CH₃ | H | 5-CH₃ | CO₂CH₃ | 5-methylfuran-2-yl | |
| 85 | C₂H₅ | C₂H₅ | H | CO₂CH₃ | 5-methylfuran-2-yl | 101–103 |
| 86 | CH₃ | CH₃ | CH₃ | CO₂CH₃ | 5-methylfuran-2-yl | |
| 87 | CH₃ | CH₃ | H | CO₂C₂H₅ | 5-methylfuran-2-yl | oil |
| 88 | CH₃ | CH₃ | H | CO₂i-C₃H₇ | 5-methylfuran-2-yl | |
| 89 | CH₃ | CH₃ | H | CO₂CH₃ | 5-bromofuran-2-yl | |
| 90 | CH₃ | CH₃ | H | CO₂CH₃ | 3,4,5-trimethylfuran-2-yl | 126–128 |
| 91 | CH₃ | CH₃ | H | CO₂CH₃ | tetrahydrofuran-2-yl | |
| 92 | CH₃ | CH₃ | H | CO₂CH₃ | isoxazol-5-yl | |
| 93 | CH₃ | CH₃ | H | CO₂CH₃ | 3,4-dimethylisoxazol-5-yl | 122 |
| 94 | CH₃ | CH₃ | H | CO₂CH₃ | 3-methylisoxazol-5-yl | 106–108 |

-continued $$\text{structure with } R^1, R^2, R^3 \text{ on benzene ring, N-CH}_2\text{-N(R}^4\text{)(CN), N-CO-R}^5$$

| Compound no. | R¹ | R² | R³ | R⁴ | R⁵ | m.p. (°C.) or $n_D^{20}$ |
|---|---|---|---|---|---|---|
| 95 | CH₃ | CH₃ | H | CO₂CH₃ | thiazolyl | |
| 96 | CH₃ | H | 4-Cl | CO₂CH₃ | furyl | |
| 97 | CH₃ | H | H | CO₂CH₃ | furyl | |
| 98 | H | CH₃ | 3-Cl | CO₂CH₃ | furyl | |
| 99 | H | Cl | H | CO₂CH₃ | furyl | |
| 100 | CH₃ | H | 5-Cl | CO₂CH₃ | CH₂OCH₃ | 95 |
| 101 | CH₃ | H | H | CO₂CH₃ | CH₂OCH₃ | 90 |
| 102 | H | Cl | H | CO₂CH₃ | CH₂OCH₃ | |
| 103 | CH₃ | C₂H₅ | H | CO₂CH₃ | CH₂OCH₃ | 1.5261 |
| 104 | CH₃ | C₂H₅ | H | CO₂C₂H₅ | CH₂OCH₃ | 1.5210 |
| 105 | CH₃ | CH₃ | 4-t.C₄H₉ | CO₂CH₃ | CH₂OCH₃ | 98 |
| 106 | CH₃ | H | 5-t.C₄H₉ | CO₂CH₃ | CH₂OCH₃ | 1.5130 |
| 107 | CH₃ | CH₃ | H | CO₂CH₃ | CH₂—CH₂OCH₃ | oil |
| 108 | CH₃ | CH₃ | H | CO₂C₂H₅ | CH₂—CH₂OCH₃ | oil |
| 109 | CH₃ | CH₃ | H | CO₂CH₃ | CH(CH₃)OCH₃ | oil |
| 110 | CH₃ | CH₃ | H | CO₂C₂H₅ | CH(CH₃)OCH₃ | 84–86 |
| 111 | CH₃ | CH₃ | H | CO₂CH₂CH=CH₂ | CH₂OCH₃ | oil |
| 112 | CH₃ | CH₃ | H | CO₂CH₂CH=CH₂ | furyl | |
| 113 | CH₃ | CH₃ | H | CO₂CH₃ | CH₂Cl | 125–128 |
| 114 | CH₃ | C₂H₅ | H | CO₂CH₃ | CH₂Cl | 61–63 |
| 115 | CH₃ | CH₃ | H | CO₂C₂H₅ | CH₂Cl | 93–95 |
| 116 | CH₃ | CH₃ | H | CO₂CH₃ | CH₂—CH₂—F | |
| 117 | CH₃ | CH₃ | H | CO₂CH₃ | oxadiazolyl | |
| 118 | CH₃ | CH₃ | H | CO₂CH₃ | methyl-oxadiazolyl | |
| 119 | CH₃ | CH₃ | H | CO₂CH₃ | methyl-thiadiazolyl | |
| 120 | CH₃ | CH₃ | H | CO₂CH₃ | thiadiazolyl | |
| 121 | CH₃ | CH₃ | H | CO₂CH₃ | chloro-thiadiazolyl | |

-continued structure:
R1, R2, R3 on phenyl ring; N attached to CH2-N(R4)(CN) and CO-R5

| Compound no. | R¹ | R² | R³ | R⁴ | R⁵ | m.p. (°C.) or $n_D^{20}$ |
|---|---|---|---|---|---|---|
| 122 | CH₃ | CH₃ | H | CO₂CH₃ | 2,6-dichloropyridin-4-yl | 143–144 |
| 123 | CH₃ | CH₃ | H | CO₂C₂H₅ | phenyl | 110 |
| 124 | CH₃ | CH₃ | H | CO₂CH₃ | 3-fluorophenyl | 136 |
| 125 | CH₃ | CH₃ | H | CO₂C₂H₅ | 3-methylphenyl | 123–124 |
| 126 | CH₃ | CH₃ | H | CO₂C₂H₅ | 2-methylphenyl | 95–97 |
| 127 | CH₃ | CH₃ | H | CO₂C₂H₅ | 3-nitrophenyl | 193 |
| 128 | CH₃ | CH₃ | H | CO₂CH₃ | 4-methoxyphenyl | 102–104 |
| 129 | CH₃ | CH₃ | H | CO₂CH₃ | 3-methoxyphenyl | 105–106 |
| 130 | CH₃ | CH₃ | H | CO₂CH₃ | 3-trifluoromethylphenyl | 108–109 |
| 131 | CH₃ | CH₃ | H | CO₂CH₃ | 3-cyanophenyl | 145–147 |
| 132 | CH₃ | CH₃ | H | CO₂CH₃ | CH₂OC₂H₅ | 76–78 |
| 133 | CH₃ | CH₃ | H | CO₂C₂H₅ | CH₂OC₂H₅ | 79 |
| 134 | CH₃ | CH₃ | H | CO₂CH₃ | furyl | oil |
| 135 | CH₃ | CH₃ | H | CO₂C₂H₅ | thienyl | 64–68 |
| 136 | CH₃ | CH₃ | H | CO₂CH₃ | isoxazolyl | 99 |

The new active ingredients are applied for instance in the form of directly sprayable solutions, powders, suspensions (including high-percentage aqueous, oily or other suspensions or dispersions), emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The new active ingredients have a strong fungitoxic action on phytopathogenic fungi, especially from the Phycomycetes class. The new compounds are therefore suitable for instance for combating *Phytophthora infestans* in tomatoes and potatoes, *Phytophthora parasitica* in strawberries, *Phytophthora cyctorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in grapes, *Plasmopara halstedii* in sunflowers, *Sclerospora macrospora* in Indian corn, *Bremia lactucae* in lettuce, *Mucor mucedo* in fruit, and *Rhizopus nigricans* in beets. The fungicidal agents contain from 0.1 to 95 wt% of active ingredient, preferably from 0.5 to 90%. The application rates depend on the type of effect desired and are from 0.1 to 5 kg of active ingredient per hectare. Some of the active ingredients have curative properties, i.e., the agents may also be applied after the plants have been infected by the pathogen, and success is still ensured. Furthermore, many of the new compounds have a systemic action, which means that visible plant parts may also be protected by a root treatment.

The new compounds may also be used to combat fungi which cause seedling and emergence diseases, e.g., Pythium and Aphanomyces species in Leguminosae and cotton. For this use, the active ingredients are applied as seed disinfectants at rates of from 10 to 200 g of active ingredient per 100 kg of seed.

The agents according to the invention may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:

manganese N,N-ethylene-bis-dithiocarbamate,
manganese zinc N,N-ethylenediamine-bis-dithiocarbamate,
the ammonia complex of zinc N,N-ethylene-bis-dithiocarbamate and N,N'-polyethylene- bis (thiocarbamoyl)-disulfide,
N-trichloromethylthiotetrahydrophthalimide, N-trichloromethylphthalimide, 5-ethoxy-3-trichloromethyl-1,2,3-thiadiazole,
2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 5-methyl-5-methoxymethyl-3-(3,5-dichlorophenyl)-2,4-dioxo-1,3-oxazolidine-N-p-fluorophenyl-2,3-di-chloromaleimide.

The following lists of fungicides with which the compounds according to the invention may be combined is intended to illustrate and not restrict the combination possibilities.

Examples of fungicides which may be combined with the compounds according to the invention are: dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithiaanthraquinone, 2-thio-1,3-dithio(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiin-4,4-dioxide, 2,3-dihydro-5-carboxanildio-6-methyl-1,4-oxathiin, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecylmorpholine and its salts, 2,6-dimethyl-N-cyclododecyl-morpholine and its salts, α-(2-chlorophenyl-α-(4-chlorophenyl)-5-pyrimidine-methanol, 1-(4-chlorophenoxy)-3,3-dimethyl-1-(1H-1,2,4-triazol-1-yl)-2-butanone, and 1-(4-chlorophenoxy)-3,3-dimethyl-1-(1H-1,2,4-triazol-1-yl)-2-butanol.

The following examples illustrate the fungicidal action of the compounds. The following prior art fungicidal compounds are used in the examples for comparison purposes:

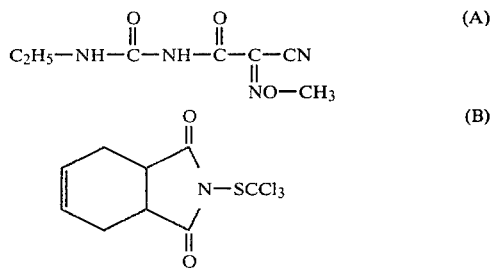

(A)

(B)

EXAMPLE 4

Fungicidal action on *Phytophthora infestans* in tomatoes

Leaves of tomato plants of the "Professor Rudloff" variety are sprayed with aqueous suspensions containing (dry basis) 80% (wt%) of active ingredient and 20% of sodium lignin sulfonate. 0.025 and 0.012% (dry basis) spray liquors are used. After the sprayed-on layer has dried, the leaves are infected with a zoospore suspension of *Phytophthora infestans*. The plants are then placed for 5 days in a steam-saturated (moist) chamber kept at 16° to 18° C. After this period, the disease has spread on the untreated control plants to such an extent that the fungicidal action of the compounds can be assessed.

| Active ingredient | Leaf attack after spraying with liquor containing active ingredients in amounts of | |
|---|---|---|
| | 0.025% | 0.012% |
| 37 | 0 | 1 |
| 56 | 0 | 0 |
| 74 | 0 | 0 |
| 80 | 0 | 1 |
| A (prior art) | 2 | 1 |
| Control (untreated) | 5 | |

0 = no fungus attack, graduated down to 5 = total attack

EXAMPLE 5

Fungicidal action on *Plasmopara viticola* in grapes

Leaves of potted vines of the Müller-Thurgau variety are infected with a zoospore suspension of *Plasmopara viticola*. The plants are then placed for 16 hours in a steam-saturated (moist) chamber at 24° C. The leaf tissue is infected during this period. To determine the curative action, the plants are then sprayed with aqueous suspensions containing (dry basis) 80% (by weight) of the active ingredient and 20% of sodium lignin sulfonate. 0.05% spray liquors (dry basis) are used. The vines are then placed for 8 days in the greenhouse at 22° to 24° C. To accelerate and intensify the sporangiophore discharge, the plants are then again placed in the moist chamber for 16 hours. Leaf attack is then assessed as follows: 0=no damage, graduated down to 5=total attack (control).

| After ingredient | Leaf attack after spraying with liquor containing active ingredients in an amount of |
|---|---|
| | 0.05% |
| 1 | 0 |
| 8 | 0 |
| 9 | 0 |
| 27 | 0 |
| 36 | 0 |
| 37 | 0 |
| 53 | 0 |
| 80 | 0 |
| 85 | 0 |
| A (prior art) | 2–3 |
| Control (untreated) | 5 |

EXAMPLE 6

Fungicidal action on emergence diseases in peas 100 g samples of pea seeds of the "Senator" variety are carefully shaken for about 5 minutes in glass bottles with 300 mg (=0.3 wt%) of seed disinfectant formulations containing (dry basis) 40% of active ingredient and 60% of clay. Subsequently, 100 seeds are sown 3 cm deep and 3 to 5 cm apart in seed boxes in a compost naturally and heavily infested with the fungi Pythium spec., Aphanomyces spec. and *Fusarium oxysporum*. The boxes are set up in the greenhouse at from 17° to 20° C. The number of healthy pea plants is determined after 21 days.

| After ingredient | Percentage of healthy plants after 21 days in compost |
|---|---|
| 74 | 90 |
| B (prior art) | 60 |
| Control (untreated) | 10 |

| After ingredient | Percentage of healthy plants after 21 days in compost |
|---|---|
| Control (sterilized compost) | 93 |

EXAMPLE 7

90 parts by weight of compound 1 is mixed with 10 parts by weight of N-methyl-α-pyrrolidone. A mixture is obtained which is suitable for application in the form of very fine drops.

EXAMPLE 8

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 10

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 12

3 parts by weight of compound 3 is intimately mixed with 97 parts by weight of particulate kaolin. A dust is obtained containing 3% by weight of the active ingredient.

EXAMPLE 13

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 15

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A substituted cyanamide of the formula

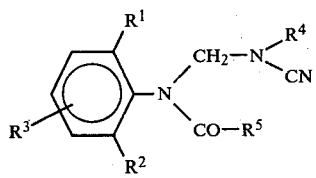

where $R^1$ denotes $C_1$–$C_4$-alkyl or $C_1$–$C_4$-alkoxy, $R^2$ denotes hydrogen, $C_1$–$C_4$-alkyl, $C_1$–$C_4$-alkoxy or halogen, $R^3$ denotes hydrogen, $C_1$–$C_4$-alkyl or halogen, $R^4$ denotes $C_1$–$C_6$-alkoxycarbonyl, $C_3$–$C_4$-alkenoxycarbonyl, $C_1$–$C_6$-alkylthiocarbonyl, or cyano, and $R^5$ denotes $C_1$–$C_6$-alkyl which is unsubstituted or substituted by lower alkoxy, alkylthio, cyano or by halogen; unsubstituted or halogen-substituted $C_2$–$C_5$-alkenyl; $C_2$–$C_4$-alkynyl; $C_3$–$C_7$-cycloalkyl; or $R^5$ denotes unsubstituted phenyl or phenyl substituted by from one to three identical or different substituents selected from the group consisting of fluorine, chlorine, bromine, trifluoromethyl, cyano, nitro, $C_1$–$C_4$-alkyl, and $C_1$–$C_4$-alkoxy.

2. A substituted cyanamide selected from the group consisting of N-methoxycarbonyl-N-(N'-methoxyacetyl, N'-2',6'-dimethylanilinomethyl)-cyanamide, N-ethoxycarbonyl-N-(N'-methoxyacetyl, N'-2',6'-dimethylanilinomethyl)-cyanamide, N-methoxycarbonyl-N-(N'-3-fluorobenzoyl, N'-2',6'-dimethylanilinomethyl)-cyanamide and N-methoxycarbonyl-N-(N'-4-fluorobenzoyl, N'-2',6'-dimethylanilinomethyl)-cyanamide.

3. A process for combating fungi, which comprises treating the fungi or the objects to be protected against fungus attack with an effectius amount of a substituted cyanamide of the formula

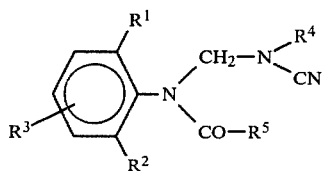

where $R^1$ denotes $C_1$–$C_4$-alkyl or $C_1$–$C_4$-alkoxy, $R^2$ denotes hydrogen, $C_1$–$C_4$-alkyl, $C_1$–$C_4$-alkoxy or halogen, $R^3$ denotes hydrogen, $C_1$–$C_4$-alkyl or halogen, $R^4$ denotes $C_1$–$C_6$-alkoxycarbonyl, $C_3$–$C_4$-alkenoxycarbonyl, $C_1$–$C_6$-alkylthiocarbonyl, or cyano, and $R^5$ denotes $C_1$–$C_6$-alkyl which is unsubstituted or substituted by lower alkoxy, alkylthio, cyano or by halogen; unsubstituted or halogen-substituted $C_2$–$C_5$-alkenyl; $C_2$–$C_4$-alkynyl; $C_3$–$C_7$-cycloalkyl; or $R^5$ denotes unsubstituted phenyl or phenyl substituted by from one to three identical or different substituents selected from the group consisting of fluorine, chlorine, bromine, trifluoromethyl, cyano, nitro, $C_1$–$C_4$-alkyl, and $C_1$–$C_4$-alkoxy.

* * * * *